United States Patent
Graff et al.

(12)

(10) Patent No.: US 6,420,399 B1
(45) Date of Patent: Jul. 16, 2002

(54) TOPICAL OPHTHALMIC MAST CELL STABILIZERS FOR TREATING ALLERGIC EYE DISEASE

(75) Inventors: Gustav Graff, Cleburne; John M. Yanni, Burleson, both of TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/527,401

(22) Filed: Mar. 16, 2000

Related U.S. Application Data

(60) Provisional application No. 60/139,945, filed on Jun. 18, 1999, and provisional application No. 60/158,177, filed on Oct. 7, 1999.

(51) Int. Cl.[7] .............................................. A61K 31/41
(52) U.S. Cl. ...................................... 514/359; 514/912
(58) Field of Search ................................ 514/359, 912

(56) References Cited

U.S. PATENT DOCUMENTS

| | | | |
|---|---|---|---|
| 4,778,814 A | 10/1988 | Cash .......................... | 514/359 |
| 4,871,865 A | 10/1989 | Lever, Jr. et al. ........... | 549/354 |
| 4,923,892 A | 5/1990 | Lever, Jr. et al. ........... | 514/450 |
| 5,192,780 A | 3/1993 | York et al. ................... | 514/357 |
| 5,641,805 A | 6/1997 | Yanni et al. ................. | 514/450 |

FOREIGN PATENT DOCUMENTS

| | | |
|---|---|---|
| EP | 0 433 766 A1 | 6/1991 |
| WO | WO 98/42353 | 10/1998 |
| WO | WO 98/56381 | 12/1998 |
| WO | WO 00/03705 | 1/2000 |
| WO | WO 00/18731 | 4/2000 |

OTHER PUBLICATIONS

Attwood et al., "The Interaction of Antihistamines with Lecithin Monolayers," *J. Pharm. Pharmac.,* vol. 27, pp. 806–810 (1975).

Brockman et al., "Interactions of Olopatadine and Ketotifen with a Phosphatidycholine Model Membrane: Investigation of Potential Mechanisms of Action," Presented at 2nd International Symposium, Leeds Castle, Kent, England, Jun. 22–25, 1999.

Fisher et al., "Blood–Brain Barrier Permeation: Molecular Parameters Governing Passive Diffusion," *J. Membrane Biol.,* vol. 165, pp. 201–211 (1998).

Gescher et al., "Correlation of Physiochemical Properties With Absorption and Metabolism of Some Tricyclic Drugs," *J. Pharm. Pharmac.,* vol. 30, pp. 353–358 (1978).

Johnson et al., "Development of New Antiallergic Drugs (Cromolyn Sodium Lodoxamide Tromethamine)," *Monogr. Allergy,* vol. 14, pp. 299–306 (1979).

Mayer et al., "Prothrombin Association with Phospholipid Monolayers," Biochemistry, vol. 22, pp. 316–321 (1983).

Momsen et al., "The Suitability of Nichrome for Measurement of Gas–Liquid Interfacial Tension by the Wilhelmy Method," J. Colloid Interface Sci., vol. 135, pp. 547–552 (1990).

Mota et al., "The Anti–Anaphylactic and Histamine–Releasing Properties of the Antihistamines. Their Effect on the Mast Cells," *Brit. J. Pharmacol,* vol. 15, pp. 396–404 (1960).

Pethica, "The Thermodynamics of Monolayer Penetration at Constant Area," Faraday Soc. Trans., vol. 51, pp. 1402–1411 (1955).

Tsujita et al., "Regulation of Carboxylester Lipase Adsorption to Surfaces. 1. Chemical Specificity," Biochemistry, vol. 26, pp. 8423–8429 (1987).

Yanni et al., "The In Vitro and In Vivo Ocular Pharmacology of Olopatadine (AL–4943A), an Effective Anti–Allergic/Antihistaminic Agent," *J. of Ocular Pharmacology and Therapeutics,* vol. 12(4), pp. 389–400 (1996).

Weimer et al., Histamine–Stimulated Cytokine Secretion from Human Conjunctival Epithelial Cells: Inhibition by the Histamine $H_1$ Antagonist Emedastinie, *Int. Arch Allergy Immunol;* vol. 115; pp. 288–293 (1998).

Yanni et al., "A Current Appreciation of Sites for Pharmacological Intervention in Allergic Conjunctivitis: Effects of New Topical Ocular Drugs," Acta Ophthalmol. Scand., vol. 77; pp. 33–37 (1999).

Shariff et al., "Human Conjunctival Epithelial Cells Express Histamine–1 Receptors Coupled to Phosphoinositide Turnover and Intracellular Calcium Mobilization: Role in Ocular Allergic and Inflammatory Diseases," *Exp. Eye. Res.* vol. 63(2); pp. 169–178 (1996).

Udell et al., Animal and Human Ocular Surface Response to a Topical Nonimmune Mast–Cell Degranulating Agent (Compound 48/80); American Journal of Ophthalmology, vol. 91; pp. 226–230 (1981).

Verin et al., Treating Severe Eye Allergy, Clinical and Experimental Allergy, vol. 28(6); pp. 44–48 (1998).

Deschenest, et al., "Assessment of the Efficacy of Olopatadine Ophthalmic Solution (0.1%) and Ketorolac Ophthalmic Solution (0.5%) in the Allergen Challenge Model," *IOVS,* vol. 39(4); p. S549 (1998).

Giovanoni, et al., "Patanol is Superior to Claritin in Reducing Ocular itching of Allergic Conjunctivitis Using the Provocative Antigen Challenge Model," *IOVS,* 49(4); p. S684 (1999).

(List continued on next page.)

*Primary Examiner*—Zohreh Fay
(74) *Attorney, Agent, or Firm*—Patrick M. Ryan

(57) ABSTRACT

Topical ophthalmic anti-allergy drugs are identified by the extent of their interaction with a phospholipid model membrane. Disclosed are topically administrable ophthalmic formulations containing amphipathic anti-allergy compounds at concentrations such that the drugs have Surface Activity Ratings from about 2–11.

2 Claims, 1 Drawing Sheet

OTHER PUBLICATIONS

Shariff et al., "Characterization of the Ocular Antiallergic and Antihistaminic Effects of Olopatadine (AL–4943A), a Novel Drug for Treating Ocular Allergic Diseases," *J. of Pharmacology and Experimental Therapeutics, US American Society for Pharmacology*, vol. 278(3); pp. 1252–1261 (1996).

Attwood et al., "The surface activity of some antihistamines at the air–solution interface," *J. Pharm. Pharmac.*, vol. 27, pp. 754–758 (1975).

Attwood et al., "The interaction of antihistamines with lecithin monolayers," *J. Pharm. Pharmac.*, vol. 27, pp. 806–810 (1975).

TOPICAL OPHTHALMIC MAST CELL STABILIZERS FOR TREATING ALLERGIC EYE DISEASE

This application claims priority from now abandoned U.S. Provisional Patent Application Serial No. 60/139,945 filed Jun. 18, 1999, and Serial No. 60/158,177, filed Oct. 7, 1999.

BACKGROUND OF THE INVENTION

1. Field of the Invention

The present invention relates to topical ophthalmic formulations used for treating allergic eye diseases, such as allergic conjunctivitis, vernal conjunctivitis, vernal keratoconjunctivitis, and giant papillary conjunctivitis. More particularly, the present invention relates to therapeutic and prophylactic topical use of mast cell stabilizers for treating and/or preventing allergic eye diseases.

2. Description of the Related Art

Conventional antihistamine drugs are known to exhibit biphasic effects on mast cells. At lower concentrations, antihistamines promote an inhibition of histamine release from mast cells. As concentrations of antihistamines are increased there is a spontaneous release of histamine from mast cells, which is associated with an apparent loss of mast cell membrane stability. See, for example, Mota et al., *Brit. J. Pharmacol.* 15:396–404. This biphasic behavior has been demonstrated for the anti-allergy drug ketotifen (4,9-dihydro-4-(1-methyl-4-piperidinyl-idene)-10H-benzo[4,5] cyclohepta-[1,2-b]thiophen-10-one) in purified preparations of human conjunctival mast cells. Yanni et al., *J. Ocular Pharmacol.*, 12:389–400 (1996).

First generation mast cell stabilizer drugs without antihistaminic activity, such as cromolyn sodium, also exhibit biphasic behavior. Johnson et al., *Monogr. Allergy*, 14:299–306 (1979).

U.S. Pat. Nos. 4,871,865 and 4,923,892, both assigned to Burroughs Wellcome Co. ("the Burroughs Wellcome Patents"), describes certain carboxylic acid derivatives of doxepin, including 11-(3-dimethylaminopropylidene)-6,11-dihydrodibenz[b,e]oxepine-2-carboxylic acid and 11-(3-dimethylaminopropylidene)-6,11-dihydrodibenz[b,e] oxepine-2(E)-acrylic acid, as mast cell stabilizers with antihistaminic action. These compounds inhibit the release of autacoids (i.e., histamine, serotonin, and the like) from mast cells and inhibit directly histamine's effects on target tissues. The Burroughs Wellcome Patents teach various pharmaceutical formulations containing the carboxylic acid derivatives of doxepin; Example 8 (I) in both of the patents discloses an ophthalmic solution formulation.

U.S. Pat. No. 5,641,805 discloses topical ophthalmic formulations for treating allergic eye diseases. The topical formulations contain acetic acid derivatives of doxepin and, in particular, Z-11-(3-dimethylaminopropylidene)-6,11-dihydrodibenz[b,e]oxepin-2-acetic acid (i.e., olopatadine), which is the cis form of the compound having the formula.

Unlike other antihistamine or mast cell stabilizer anti-allergy drugs, olopatadine does not provoke a release of histamine from mast cells at concentrations higher than those for which antihistaminic activity is observed. Other topical ocular anti-allergy drugs that maintain mast cell membrane stability and prevent histamine release from mast cells over a drug concentration range of 0.01–0.5% (w/v) are desired.

SUMMARY OF THE INVENTION

The present invention provides a method for selecting anti-allergy drug concentrations that are suitable for use in the topical treatment of allergic eye diseases. According to the present method, an amphipathic anti-allergy compound's Surface Activity Rating is determined as described below. For topically administrable ophthalmic anti-allergy products, the anti-allergy drug concentration is chosen so that the drug has a Surface Activity Rating (in units of mN/m) from about 2–11.

The present invention is also directed toward topically administrable ophthalmic anti-allergy pharmaceutical drug products comprising an amphipathic anti-allergy drug at a concentration such that the drug has a Surface Activity Rating from about 2–11.

Among other factors, the present invention is based on the finding that amphipathic anti-allergy compounds formulated at concentrations at which they have a Surface Activity Rating of greater than 11 are likely to cause mast cell membrane instability and leakage of autocoids, including histamine, from human conjunctival mast cells.

DETAILED DESCRIPTION OF THE INVENTION

Figure 1:
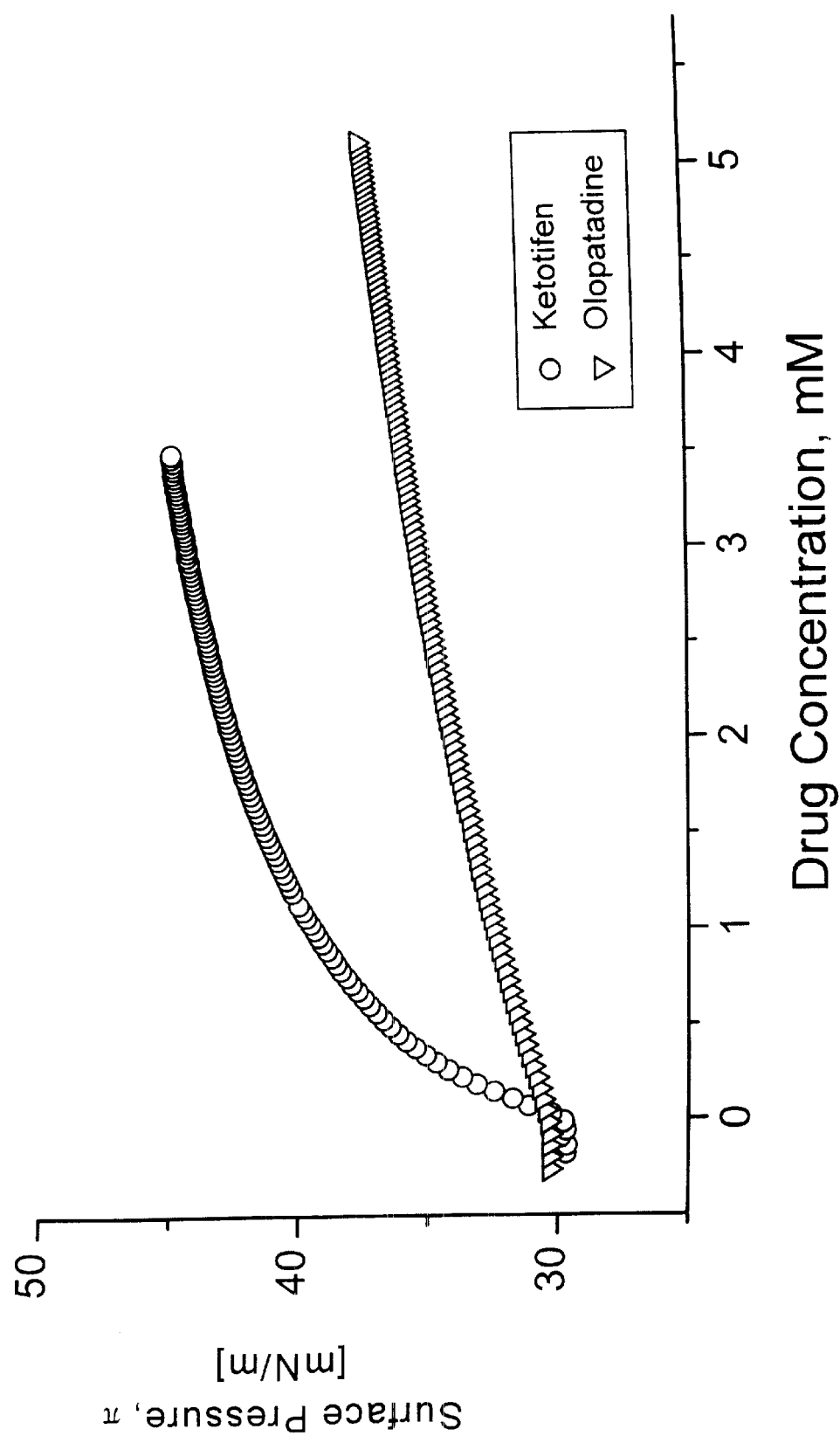
FIG. 1 shows the effect of olopatadine and ketotifen drug concentrations on the surface pressure of 1-stearoyl-2-oleoyl-sn-glycero-3-phosphocholine (SOPC) monolayers spread at an initial surface pressure of 30 mN/m.

According to the present invention, topically administrable ophthalmic anti-allergy pharmaceutical drug products comprise an amphipathic anti-allergy drug at a concentration such that the drug has a Surface Activity Rating from about 2–11, and preferably from about 4–11. The drug products of the present invention contain an amphipathic anti-allergy drug at a concentration of about 20 mM or less.

The Surface Activity Rating is obtained by determining the interaction of an amphipathic anti-allergy drug ("test compound") in buffer alone with a phospholipid monolayer. Test compound/mast cell membrane interaction is mimicked in a phospholipid monolayer spread onto an aqueous buffer in a modified Langmuir trough. In this system, test compound-membrane interaction is quantified by determining the change in surface pressure ($\Delta\pi$ in mN/m) of a monomolecular film of 1-stearoyl-2-oleoyl-sn-glycero-3- phosphocholine (SOPC) spread at an initial surface pressure of 28–32 mN/m on an aqueous buffer sub-phase. The initial surface pressure of 28–32 mN/m is chosen because this pressure mimics that of most mammalian cell membranes.

Surface pressure changes are measured at 24° C., while progressively increasing the concentration of test compound in the buffer sub-phase from 0 to at least 5 mM (or to the compound's solubility limit if less than 5 mM), and preferably to at least 20 mM (or the compound's solubility limit if less than 20 mM). Test compound is added to the sub-phase by continuous sub-phase exchange (keeping the total volume of the sub-phase constant) at a rate slow enough to avoid disturbing the SOPC monolayer (0.4 ml/min., for example).

Surface pressure is measured using an automated interfacial monitor-controller built around a Cahn 27 electrobalance equipped with a 24 ga. nichrome wire Wilhelmy probe. [See Tsujita et al, Regulation of carboxylester lipase adsorption to surfaces. 1. Chemical specificity. *Biochemistry* 26:8423–8429 (1987) and Momsen et al., The suitability of nichrome for measurement of gas-liquid interfacial tension by the Wilhelmy method. *J. Colloid Interface Sci.* 135:547–552 (1990).] The two aqueous compartments (circular and rectangular) of the keyhole-shaped Teflon trough are disconnected; only the circular compartment (area=25.5 cm$^2$, volume=24.4 ml) is used for monolayer formation. Temperature in both compartments is maintained at 24° C. using a thermostated base plate controlled by a precision water bath. Precise positioning of the Wilhelmy probe in the aqueous phase, correction for probe buoyancy due to immersion, sub-phase stirring, and data collection are controlled by microprocessor (Tsujita et al, id.).

The effect of test compound on surface pressure is determined by a continuous exchange of the aqueous phase with a concentrated solution of the test compound in buffer. Although the identity of the buffer is not critical as long as the aqueous sub-phase is maintained at a physiological pH, the preferred buffer is 10 mM HEPES/100 mM NaCl with the pH adjusted to 7.5. The concentration of test compound in the aqueous phase is determined from the fraction of sub-phase volume exchanged and the concentration of the solute in the concentrated solution. The continuous exchange is necessary to avoid disturbing the SOPC monolayer, and is accomplished by a side or bottom injection/withdrawal ports.

The amphipathic anti-allergy drugs of the present invention preferably possess antihistamine activity, such as tricyclic H$_1$-receptor antagonists exhibiting an in vitro binding affinity (k$_i$) in the range of 0.1–100 nM for the H$_1$-receptor. The amphipathic anti-allergy drugs of the present invention exclude olopatadine, ketotifen, emedastine, pheniramine, pyrilamine, cromolyn, nedocromil and levocabastine.

Formulations of the anti-allergy compounds for topical ophthalmic administration can be made using known techniques. Ophthalmically acceptable excipients, such as tonicity-adjusting agents, pH-adjusting agents, buffering agents, preservatives, comfort enhancing agents, viscosity-modifying agents, stabilizing agents, etc. may be included. For example, sodium chloride, glycerin, mannitol or the like may be used as the isotonic agent; p-hydroxybenzoic acid ester, benzalkonium chloride or the like as the preservative; sodium hydrogenphosphate, sodium dihydrogenphosphate, boric acid or the like as the buffering agent; sodium edetate or the like as the stabilizer; polyvinyl alcohol, polyvinyl pyrrolidone, polyacrylic acid or the like as the viscous vehicle; and sodium hydroxide, hydrochloric acid or the like as the pH controller. If desired, formulations containing the anti-allergy agents according to the present invention may also contain other active agents.

Eye drop formulations produced according to the present invention will typically need only be applied to the eyes from once to a few times a day in an amount of one to several drops at a time, though in more severe cases the drops may be applied several times a day. A typical drop is about 30 μl.

Certain embodiments of the invention are illustrated in the following examples.

EXAMPLE 1

Topical Ophthalmic Solution Formulation

| Ingredient | Concentration (W/V%) |
| --- | --- |
| Compound having a Surface Activity Rating ≦ 11.2 at the selected concentration | 0.01–0.5 |
| Dibasic Sodium Phosphate (Anhydrous), USP | 0.5 |
| Sodium Chloride, USP | 0.65 |
| Benzalkonium Chloride | 0.01 |
| Sodium Hydroxide, NF | q.s. pH = 7.0 |
| Hydrochloric Acid, NF | q.s. pH = 7.0 |
| Purified Water | q.s. 100 |

EXAMPLE 2

Topical Ophthalmic Gel Formulation

| Ingredient | Concentration (W/V%) |
| --- | --- |
| Compound having a Surface Activity Rating ≦ 11.2 at the selected concentration | 0.01–0.5 |
| Carbopol 974 P | 0.8 |
| Edetate Disodium | 0.01 |
| Polysorbate 80 | 0.05 |
| Benzalkonium Chloride, Solution | 0.01 + 5 xs |
| Sodium Hydroxide | q.s. pH 7.2 |
| Hydrochloric acid | q.s. pH 7.2 |
| Purified Water | q.s. 100 |

EXAMPLE 3

Measurement of the Surface Activity Rating of Olopatadine and Ketotifen

Water was purified by reverse osmosis and carbon filtration, passage through an Elix 3 deionization system (Millipore) and passage through a Milli Q UV Plus polishing system (Millipore). Buffer, comprised of 10 mM HEPES containing 0.1M NaCl pH 7.5, was used to prepare solutions of olopatadine and ketotifen (and for control experiments). After mixing the drug with the buffer, it was necessary to readjust the pH to a value of 7.5 with 5 M NaOH. All chemicals were reagent grade.

Exchange of Aqueous Phase Contents

The circular compartment of the automated interfacial monitor-controller described above was fitted with an inlet tube (1/32" ID Teflon) and an outlet tube (18 ga. Teflon) which entered through the outer wall of the sample compartment. These were connected to 25-mL, gas-tight syringes (model 1025, Hamilton, Reno, Nev.) mounted in a microprocessor-controlled push-pull dual syringe pump (model sp260p, World Precision Instruments, Sarasota, Fla.) through three-way Teflon valves (Hamilton, Reno, Nev.)

which were used for filling and flushing. About 42 cm of the inlet tube was coiled in the water-filled rectangular compartment of the trough in order to equilibrate the incoming solution to the temperature of the circular compartment. A custom Teflon-coated magnetic stirring bar (length=3.6 cm, diameter 2 mm) was used to mix the aqueous contents. The bar was at approximately 50 rpm by stepper motor-driven magnet mounted beneath the circular compartment and controlled by the microprocessor. The relatively slow stirring speed and small bar diameter were used to minimize disturbance of the lipid monolayer. To exchange the contents of the circular compartment with the solution in the inlet syringe while maintaining constant volume, the syringes were operated in unison, but in opposite directions, by the syringe pump. Control experiments showed that, during exchange of 25 ml of aqueous phase, the volume of liquid removed from a test container remained constant to within an average deviation of 0.023 ml (n=2), or ~0.1%. This insured that the depth of immersion of the Wilhelmy probe was constant to within ~10 $\mu$m and, hence, the contact angle of the aqueous phase with the probe, remained essentially constant during exchange experiments.

Measurement of Olopatadine's and Ketotifen's Effect on Surface Pressure

Saturated solutions of olopatadine and ketotifen, respectively, were prepared for each exchange experiment by gently warming an excess of drug in buffer, adjusting the pH to 7.5 and equilibrating the sample to 24° C. Following filtration to remove undissolved drug, drug concentration in the solution was determined spectrophotometrically. The concentration of drug in diluted aliquots of the solution was determined by comparing their absorbance to a standard curve obtained with standard solutions of the drug. This solution or buffer (control) was loaded into the injection syringe of the apparatus and a monolayer of SOPC was spread onto the surface of the aqueous phase in the exchange compartment to slightly below the desired surface pressure of 30 mN/m. The lipid film was equilibrated for 90 to 220 min. in order to achieve a surface pressure drift rate of <0.01%/min, which was considered stable. Once the monolayer was stable, the exchange was carried out at a constant rate of 0.4 m/min during which surface pressure was recorded as a function of time.

At least duplicate exchange and control (without drug) experiments were conducted. Each set of controls was normalized to the nominal pressure and the traces were averaged. The results are shown in FIG. 1, where drug concentration vs. the surface pressure of the SOPC monolayer is plotted for each drug. Olopatadine caused a relatively small increase in surface pressure (7.1 mN/m) as its concentration in the aqueous sub-phase is increased from 0 to 5 mM. In contrast, ketotifen produced a two-fold greater increase in surface pressure (15 mN/m) than olopatadine when tested over a concentration range of 0–3.5 mM. Thus, the Surface Activity Rating of olopatadine is 7.1 and of ketotifen is 15.

What is claimed is:

1. In a topically administrable ophthalmic pharmaceutical composition comprising an ophthalmically acceptable, amphipathic, antihistamine drug at a concentration of about 20 mM or less, the improvement wherein the drug concentration is such that the drug has a Surface Activity Rating from about 2–11, provided the drug is not selected from the group consisting of olopatadine; ketotifen; emedastine; pheniramine; pyrilamine; cromolyn; nedocromil; and levocabastine.

2. The composition of claim 1 wherein the drug has a Surface Activity Rating from 4–11.

* * * * *